United States Patent [19]
Keimel

[11] Patent Number: 6,091,986
[45] Date of Patent: Jul. 18, 2000

[54] METHOD AND APPARATUS FOR STORAGE OF PHYSIOLOGIC SIGNALS

[75] Inventor: John G. Keimel, North Oaks, Minn.

[73] Assignee: Medtronic, Inc., Minneapolis, Minn.

[21] Appl. No.: 09/067,159

[22] Filed: Apr. 27, 1998

[51] Int. Cl.[7] .................................................. A61B 5/04
[52] U.S. Cl. ............................................................ 600/515
[58] Field of Search .................................. 600/301, 325, 600/327, 341, 515, 523, 544, 546, 549; 607/16–26

[56] References Cited

U.S. PATENT DOCUMENTS

| | | |
|---|---|---|
| 4,223,678 | 9/1980 | Langer et al. . |
| 4,295,474 | 10/1981 | Fischell . |
| 4,375,817 | 3/1983 | Engle et al. . |
| 4,384,585 | 5/1983 | Zipes . |
| 4,428,378 | 1/1984 | Anderson et al. . |
| 4,513,743 | 4/1985 | Kornelis et al. . |
| 4,548,209 | 10/1985 | Wielders et al. . |
| 4,577,633 | 3/1986 | Berkovits et al. . |
| 4,587,970 | 5/1986 | Holley et al. . |
| 4,688,573 | 8/1987 | Alt . |
| 4,693,253 | 9/1987 | Adams . |
| 4,726,380 | 2/1988 | Vollmann et al. . |
| 4,800,883 | 1/1989 | Winstrom . |
| 4,830,006 | 5/1989 | Haluska et al. . |
| 4,880,005 | 11/1989 | Pless et al. . |
| 4,903,701 | 2/1990 | Moore et al. . |
| 4,949,719 | 8/1990 | Pless et al. . |
| 4,949,730 | 8/1990 | Cobben et al. . |
| 4,953,551 | 9/1990 | Mehra et al. . |
| 5,086,772 | 2/1992 | Larnard et al. . |
| 5,088,488 | 2/1992 | Markowitz et al. . |
| 5,117,824 | 6/1992 | Keimel et al. . |
| 5,127,404 | 7/1992 | Wyborny et al. . |
| 5,163,427 | 11/1992 | Keimel . |
| 5,188,105 | 2/1993 | Keimel . |
| 5,222,503 | 6/1993 | Ives et al. ............................... 600/544 |
| 5,324,315 | 6/1994 | Grevious . |
| 5,330,513 | 7/1994 | Nichols et al. . |
| 5,342,402 | 8/1994 | Olson et al. . |
| 5,350,411 | 9/1994 | Ryan et al. . |
| 5,513,645 | 5/1996 | Kroiss et al. . |
| 5,522,850 | 6/1996 | Yomtov et al. .............................. 607/5 |
| 5,535,752 | 7/1996 | Halperin et al. . |
| 5,545,186 | 8/1996 | Olson et al. . |
| 5,564,434 | 10/1996 | Halperin et al. ......................... 600/549 |
| 5,730,141 | 3/1998 | Fain et al. . |

FOREIGN PATENT DOCUMENTS

| | | |
|---|---|---|
| 0554208 | 8/1993 | European Pat. Off. . |
| 0761255 | 12/1997 | European Pat. Off. . |
| 9735516 | 2/1997 | WIPO . |

OTHER PUBLICATIONS

"Onset and Stability for Ventricular Tachyarrhythmia Detection in an Implantable Pacer–Cardioverter–Defibrillator" by Olson et al., published in *Computers in Cardiology*, Oct. 7–10, 1986, IEEE Computer Society Press, pp. 167–170.

*Primary Examiner*—Jeffrey R. Jastrzab
*Attorney, Agent, or Firm*—Reed A. Duthler; Harold R. Patton

[57] ABSTRACT

An alternative mechanism in an implantable device for meeting the physician's need for a stored electrogram and/or other stored physiologic signal associated with a detected arrhythmic or other physiological event without the undesirable current drain associated with continuous operation of a sense amplifier and a looping memory. The device regularly but intermittently activates a sense amplifier or other sensor and associated memory circuitry, independent of detection of arrhythmias. The device may temporarily store only a single record, replacing it with new records as they are stored, or may store multiple records, replacing the oldest stored record with the newest stored record. On detection of an arrhythmia or other defined physiological event, the device may simply transfer the one or more temporarily stored electrogram strips to permanent storage, for later use by the physician in diagnosing the condition of the patient prior to detection of the event.

12 Claims, 3 Drawing Sheets

6,091,986

METHOD AND APPARATUS FOR STORAGE OF PHYSIOLOGIC SIGNALS

BACKGROUND OF THE INVENTION

This invention relates generally to an apparatus and method for storing electrograms and more particularly to the implementation of such a device in the context of an implantable cardioverter/defibrillator.

Implantable cardioverter/defibrillators and pacemakers have for some time included the capability of storing digitized cardiac electrograms for diagnostic purposes. Most commonly, such electrograms are stored in conjunction with the detection of cardiac arrhythmias, and include the period of time immediately preceding detection of the arrhythmia. For example, the device disclosed in U.S. Pat. No. 4,223,678 issued to Langer et al and the device disclosed in U.S. Pat. No. 4,295,474 issued to Fischell, both employ looping memories to continually store cardiac electrograms, with the contents of the looping memory being frozen on occurrence of an arrhythmic event and transferred to permanent storage. The devices also store electrograms following either detection of the arrhythmic event or delivery of an anti-arrhythmic therapy. While this approach to electrogram storage does provide the physician with information associated with the detected arrhythmia and its treatment, it has the drawback of requiring continuous operation of the looping memory and the sense amplifier, increasing the current drain on the battery and shortening the potential lifespan of the device.

Prior approaches to reducing the current drain associated with electrogram storage have focused on the storage of markers indicative of heart paced or sensed heart depolarizations and/or intervals between depolarizations and on design of low power sense amplifiers. While these approaches have been somewhat successful, the information stored in the form of markers or interval is not always adequate for diagnostic purposes and continuous activation of even low power sense amplifiers in conjunction with looping memories still results in an undesirably high current drain.

SUMMARY OF THE INVENTION

The present invention provides an alternative mechanism for meeting the physician's need for a stored electrogram and/or other stored physiologic signal associated with a detected arrhythmic event without the undesirable current drain associated with continuous operation of a sense amplifier and a looping memory. The present invention accomplishes this goal by regularly but intermittently activating a sense amplifier and associated memory circuitry, independent of detection of arrhythmias. For example, five seconds of an electrogram (EGM) might be temporarily stored every fifteen minutes or once a minute, providing a substantial reduction in current drain as compared to continuous operation of a sense amplifier and a looping memory. The device may temporarily store only a single electrogram record, replacing it with new electrogram records as they are stored, or may store multiple electrogram records, replacing the oldest stored record with the newest stored record. On detection of an arrhythmia, the device may simply transfer the one or more temporarily stored electrogram strips to permanent storage, for later use by the physician in diagnosing the heart rhythm history of the patient prior to detection of the arrhythmia. While a continuous recording of cardiac events leading to detection of an arrhythmia may not be included in the stored electrogram records, it is believed that stored information with regard to intervals between the detected depolarizations and other stored information in conjunction with the previously stored electrogram records can provide adequate diagnostic information to the physician. As an alternative or in addition to storage of electrogram records, the device may also store records of other measured physiologic parameters such as pressure, oxygen saturation, temperature and the like.

In addition, the device may also permanently store electrogram and/or other physiologic records at regular intervals, even in the absence of detected arrhythmias. For example, a temporarily stored electrogram record may be permanently stored once every day, once every week or the like, to provide the physician with an electrogram history.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENTS

Figure 1:
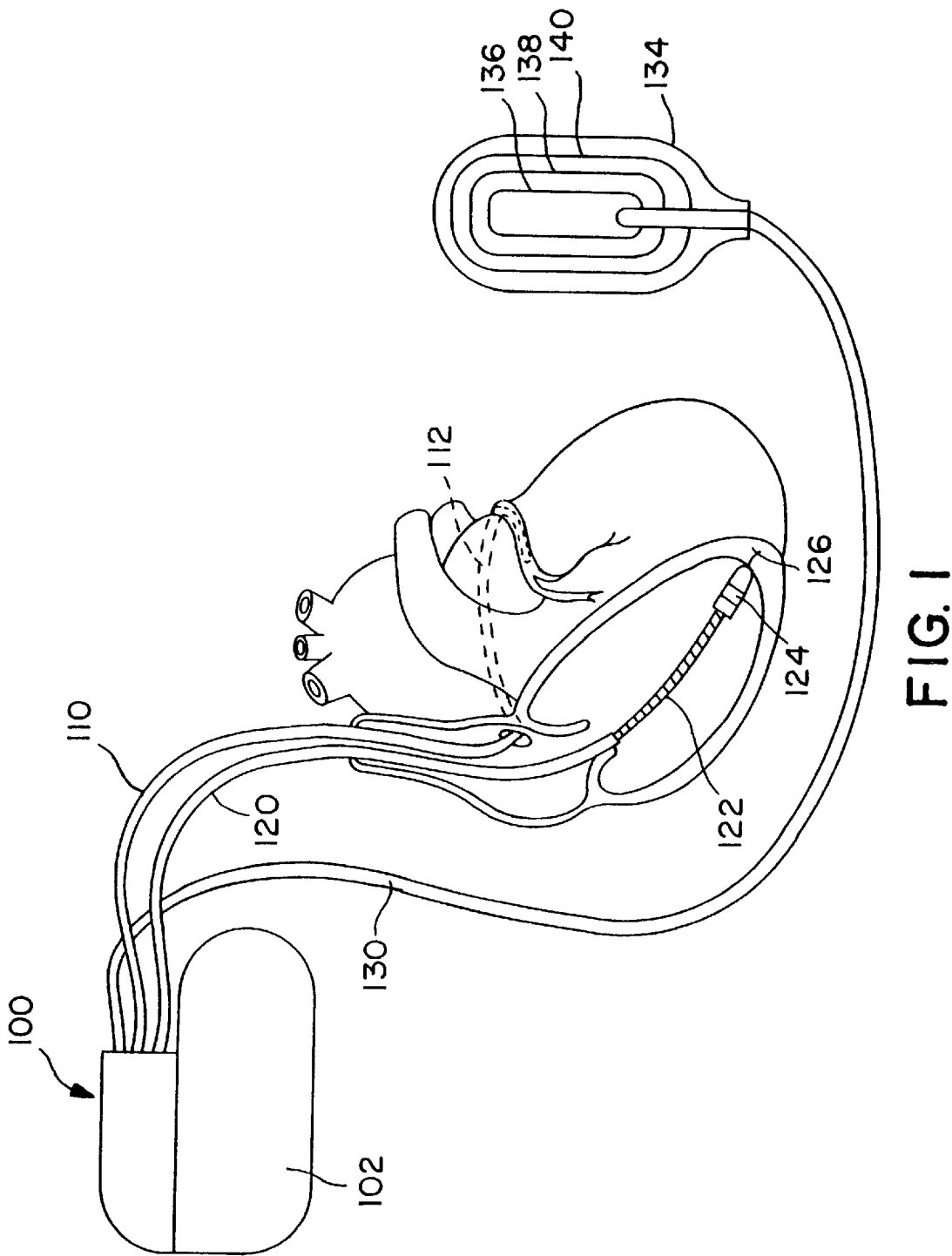
FIG. 1 is a representation of the heart, and an implanted electrode lead system, illustrating the a device embodying the present invention.

FIG. 1 illustrates an implantable cardioverter/defibrillator system of the type appropriate for use in conjunction with the present invention. The implantable defibrillator 100 is enclosed in a hermetic housing 102 which carries a battery an circuitry adapted to detect and treat tachyarrhythmias. The circuitry within housing 102 includes the circuitry embodying the present invention. The implantable cardioverter/defibrillator 100 is coupled to the heart by means of three electrode leads 110, 120 and 130 which are exemplary of typical cardioversion/defibrillation electrodes. Lead 110 includes a single elongated electrode 112 which may be located in the coronary sinus/great vein as shown or may alternately be located in the superior vena cava or subclavian vein. Lead 120 includes an elongated defibrillation electrode 122 located in the right ventricle and pacing sensing electrodes 124 and 126. Lead 130 is a subcutaneous lead which carries coil electrodes taking the form of loops, 136, 138 and 140 mounted to an insulative electrode pad 134. In alternative embodiments, the conductive housing 102 of the implantable cardioverter/defibrillator 100 may be substituted as an electrode for lead 130. Any other conventional cardioversion/defibrillation and pacing/sensing electrodes may also be employed in conjunction with a device embodying the present invention, including those employed for atrial defibrillation and dual chamber defibrillation.

Figure 2:
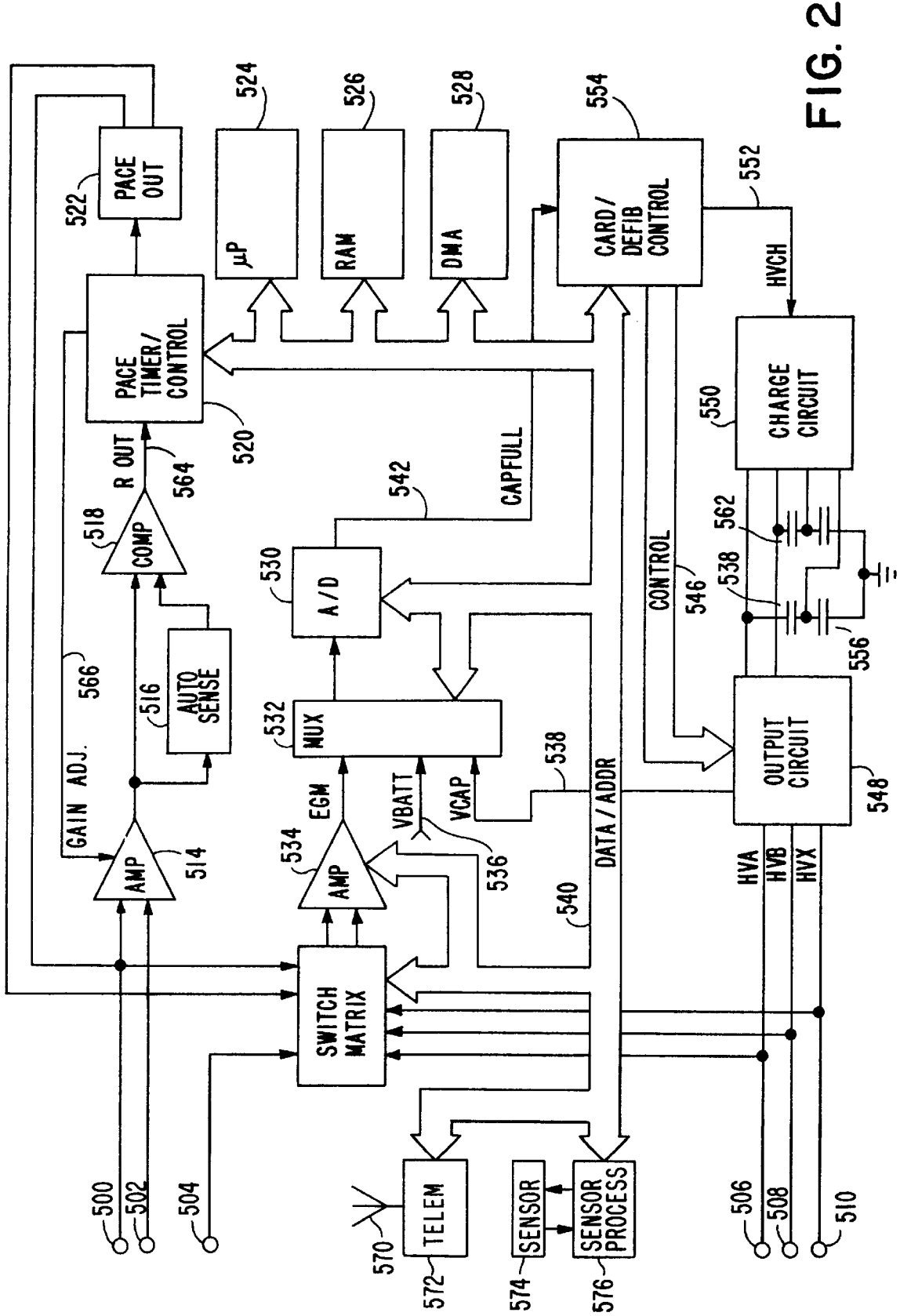
FIG. 2 is a schematic block diagram illustrating the structure of one embodiment of an implantable pacemaker/cardioverter/defibrillator in which the present invention may be embodied.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/cardioverter/defibrillators presently being implanted for clinical evaluation in the United States. The invention is also believed practicable in conjunction with implantable pacemaker/cardioverter/defibrillators as disclosed in prior U.S. Pat. Nos. 4,548,209, to Wielders et al., 4,693,253, to Adams et al., 4,830,006, to Haluska et al, 4,830,006, to Haluska et al. and 4,949,730, to Pless et al., all of which are incorporated herein by reference in their entireties.

The device is illustrated as being provided with six electrodes, 500, 502, 504, 506, 508 and 510. Electrodes 500 and 502 may be a pair of closely spaced electrodes located in the ventricle, for example, corresponding to electrodes 124 and 126 in FIG. 2. Electrode 504 may correspond to a remote, indifferent electrode located on the housing of the implantable pacemaker/cardioverter/defibrillator. Electrodes 506, 508 and 510 may correspond to the large surface area defibrillation electrodes located on the ventricular, coronary sinus and subcutaneous leads illustrated in FIG. 2 or to the epicardial electrodes 204,206 and 208 of FIG. 3.

Electrodes 500 and 502 are shown as hard-wired to the near field, R-wave detector circuit, comprising bandpass filtered amplifier 514, auto threshold circuit 516 (for providing an adjustable sensing threshold as a function of the measured R-wave amplitude) and comparator 518. A signal is generated on ROUT line 564 whenever the signal sensed between electrodes 500 and 502 exceeds the present sensing threshold defined by auto threshold circuit 516. As illustrated, the gain on the band pass amplifier 514 is also adjustable by means of a signal from the pacer timing and control circuitry 520 on GAIN ADJ line 566.

The threshold adjustment circuit 516 sets a threshold corresponding to a predetermined percentage of the amplitude of a sensed R-wave, which threshold decays to a minimum threshold level over a period of less than three seconds thereafter, as described in U.S. Pat. No. 5,117,824, issued to Keimel and incorporated herein by reference in its entirety. The time constant of the threshold circuit is also preferably sufficiently short so that minimum sensing threshold may be reached within 1–3 seconds following adjustment of the sensing threshold equal to 70–80% of the amplitude of a detected spontaneous R-wave.

In any case, each successive R-wave sense event signal on the ROUT line is routed through the pacer/timer control circuit block 520 on data bus 540 to the microprocessor 524, where it operates as an interrupt commencing a number of operations as described further below. It will be understood that the alternative sense amplifiers described above may be substituted for bandpass filtered amplifier 514, auto threshold circuit 516.

Switch matrix 512 is used to select which of the available electrodes are employed for sensing electrograms for storage according to the present invention. The electrode pair so employed may comprise electrodes 502 and 500 or electrode 500 in conjunction with one of the electrodes 504, 506, 508 or 510, or may comprise other combinations of the illustrated electrodes, including combinations of the large surface defibrillation electrodes 506, 508, 510. Selection of which two electrodes are employed is controlled by the microprocessor 524 via data/address bus 540. EGM signals from the selected electrodes are passed through bandpass amplifier 534 and into multiplexer 532, where they are converted to multi-bit digital signals by A/D converter 530, for temporary storage in random access memory 526 under control of direct memory address circuit 528. Temporary storage of a series of EGM records encompassing several seconds each is preferred, with the most recently stored record being written over the oldest temporarily stored record. In response to detection of an arrhythmia or expiration of a pre-set time period, one or more of the records is permanently stored elsewhere in memory 526 as described below.

Optionally, the device may employ a physiologic sensor 574, which may be a pressure sensor, an oxygen sensor, an activity sensor, a temperature sensor or other physiologic sensor as disclosed in as disclosed in U.S. Pat. No. 4,903,701, issued to Moore, U.S. Pat. No. 5,535,752, issued to Halperin et al., U.S. Pat. No. 4,428,378, issued to Anderson et al. and U.S. Pat. No. 4,688,573, issued to Alt, all incorporated herein by reference in their entireties. The sensor 574 may be employed to regulate pacing rate, as a part of the arrhythmia detection method employed by the devise, or simply for monitoring purposes. The sensor is controlled by microprocessor 524 via sensor processing circuitry 576, and the digitized output of the sensor is provided to data/address bus 540, so that it also can be stored in memory 526.

Communication with the device is accomplished via antenna 570 and associated telemetry circuitry 572, which may correspond to any of the various telemetry systems employed by implantable devices. For example, telemetry systems as disclosed in U.S. Pat. No. 5,350,411, issued to Ryan, U.S. Pat. No. 5,324,315, issued to Grevious, U.S. Pat. No. 5,088,488, issued to Markowitz et al. and U.S. Pat. No. 5,127,404, issued to Wyborny et al., all incorporated herein by reference in their entireties may be employed to receive commands from external programmers and to transmit stored EGM records, sensor records, operational parameters and information regarding the detection of arrhythmia by the device to an external programmer.

At defined time intervals, for example once a minute or once every 15 minutes, the microprocessor activates the band-pass amplifier 534 and temporarily stores an EGM and/or a sensor record extending over a pre-defined time period, e.g. five seconds. As discussed above, one or more such records may be temporarily stored. In response to detection of an arrhythmia, or optionally also in response to expiration of a defined longer time period, e.g. one day or one week, the microprocessor initiates permanent storage of one or more of the temporarily stored digitized EGM and/or sensor records.

In conjunction with the operation of the device, the microprocessor preferably also triggers temporary storage of the time intervals separating sensed depolarizations of the heart in response to the detected depolarizations, in the same manner as present commercially available implantable cardioverter defibrillators. These stored intervals may also be permanently stored in response to detection of an arrhythmia, to be used in conjunction with previously stored EGM records.

As discussed above, switch matrix 512 selects which of the various electrodes are coupled to band pass amplifier 534. Amplifier 534 may be a broad band pass amplifier, having a band pass extending for approximately 0.5 to 200 hertz. The filtered EGM signal from amplifier 534 is passed through multiplexer 532, and digitized in A/D converter circuitry 530. For purposes of the present invention, a sampling rate of 256 to 512 samples per second should be sufficient, although somewhat lower or substantially higher sampling rates may be used, depending on the amount of data storage capacity in RAM 526 and on the processing speed of microprocessor 524. The sampled and digitized data is stored in random access memory 526 under control of direct memory address circuitry 528.

The arrhythmia detection criteria employed by the microprocessor 526 may include sustained high rate, onset and irregularity in the heart beat rate of the patient as described above. Other variations on the arrhythmia detection criteria may be employed in the practice of the present invention and are not repeated here. Such detection algorithms for recognizing tachycardias are also described in the above cited '380 patent, U.S. Pat. No. 4,880,005, issued to Pless et al and the '006 patent, incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated by reference in its entirety herein. However, other criteria may also be measured and employed in conjunction with the present invention, including those disclosed in U.S. Pat. No. 5,545,186, issued to Olson et al., U.S. Pat. No. 5,342,402, issued to Olson et al., U.S. Pat. No. 5,086,772, issued to Larnard et al. and U.S. Pat. No. 5,730,141, issued to Fain et al., all incorporated herein by reference in their entireties may also be employed.

The remainder of the circuitry of FIG. 7 is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of bandpass amplifier, under control of microprocessor 524.

During VVI mode pacing, the escape interval counter within pacer timing/control circuitry 520 is reset upon sensing of an R-wave as indicated by a signal on line 564, and on time-out triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the tachycardia/defibrillation discrimination function.

Microprocessor 524 includes therein a read only memory which contains programming information controlling its operation. Microprocessor 524 operates as an interrupt driven device, and responds to interrupts from pacer timing/control circuitry 520 corresponding to the occurrence of sensed R-waves (as described above) and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an anti-tachyarrhythmia pacing therapy regimen is desired, appropriate timing intervals for controlling generation of anti-tachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters to in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in U.S. Pat. No. 5,188,105, to Keimel, and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585 to Zipes, in U.S. Pat. No. 4,949,719 to Pless et al., cited above, and in U.S. Pat. No. 4,375,817 to Engle et al., all incorporated herein by reference in their entireties may also be employed.

Similarly, known circuitry for controlling the timing and generation of anti-tachycardia pacing pulses as described in U.S. Pat. Nos. 4,577,633 to Berkovits et al., 4,880,005 to Pless et al., 4,726,380 to Vollmann et al., and 4,587,970 to Holley et al., all of which are incorporated herein by reference in their entireties may also be used.

Selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in commonly assigned, co-pending patent application Ser. No. 07/612,758, filed by Keimel, for an Apparatus for Delivering Single and Multiple Cardioversion and Defibrillation Pulses, filed Nov. 14, 1990, and issuing Nov. 17, 1992 as U.S. Pat. No. 5,163,427, incorporated herein by reference in its entirety. However, output control circuitry as disclosed in U.S. Pat. No. 4,953,551 to Mehra et al. or U.S. Pat. No. 4,800,883 to Winstrom, both incorporated herein by reference in their entireties, may also be used in the context of the present invention. Alternatively single monophasic pulse regimens employing only a single electrode pair according to any of the above cited references which disclose implantable cardioverters or defibrillators may also be used.

In modern implantable pacemaker/cardioverter/ defibrillators, the particular therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Therapies for fast ventricular tachycardia may be of the same general types provided in conjunction with detection of ventricular tachycardia at 616 (FIG. 8), and may include anti-tachycardia pacing and cardioversion pulse therapies. However, the therapy menu for fast ventricular tachycardia will be more aggressive than the therapy set for slower ventricular tachycardias. For example, fewer or no attempts at anti-tachycardia pacing may be undertaken prior to delivery of cardioversion pulses. Higher amplitude cardioversion pulses may be specified.

Prior art patents illustrating such pre-set therapy menus of anti-tachyarrhythmia therapies include the above-cited '006, '380 and '970 patents. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In the event that an aggressive therapy is needed, the typical therapy will be delivery of a high amplitude defibrillation pulse, typically in excess of 10 joules, and in some cases as much as 35 joules or more. As in the case of currently available implantable pacemaker/cardioverter/ defibrillators, and as discussed in the above-cited references, it is envisioned that the amplitude of the defibrillation pulse may be incremented in response to failure of an initial pulse or pulses to terminate fibrillation.

After delivery of a tachycardia therapy the arrhythmia detection criteria are again monitored. As discussed in the above-cited patents, in some cases it is desirable to have a different standard for re-detection of a tachyarrhythmia than for initial detection of the tachyarrhythmia. Typically the criteria for re-detection will be less stringent than for initial detection, and, in the present invention, the threshold index value may be reduced. Similarly, the microprocessor updates the therapy schedule, to reflect that the previously scheduled therapy had been delivered. As discussed above, in current implantable pacemaker/cardioverter/defibrillators, this generally results in the delivery of a more aggressive therapy upon re-detection of tachycardia. After updating the tachyarrhythmia related functions, the microprocessor returns the device to VVI mode bradycardia pacing and awaits the next R-wave sense event interrupt.

If a tachyarrhythmia was detected previously, the microprocessor checks to determine whether a series of R—R intervals, including the most recent, indicates a return to sinus rhythm or termination of a previously detected arrhythmia. The criterion of detection of return to sinus rhythm may be a series of a predetermined number of sequential R—R intervals which are greater than the tachycardia detection interval (TDI), for example. Following termination detection, the counters, detection methodologies and therapy schedules are all appropriately updated, and the device returns to VVI mode pacing, as discussed above.

Figure 3:
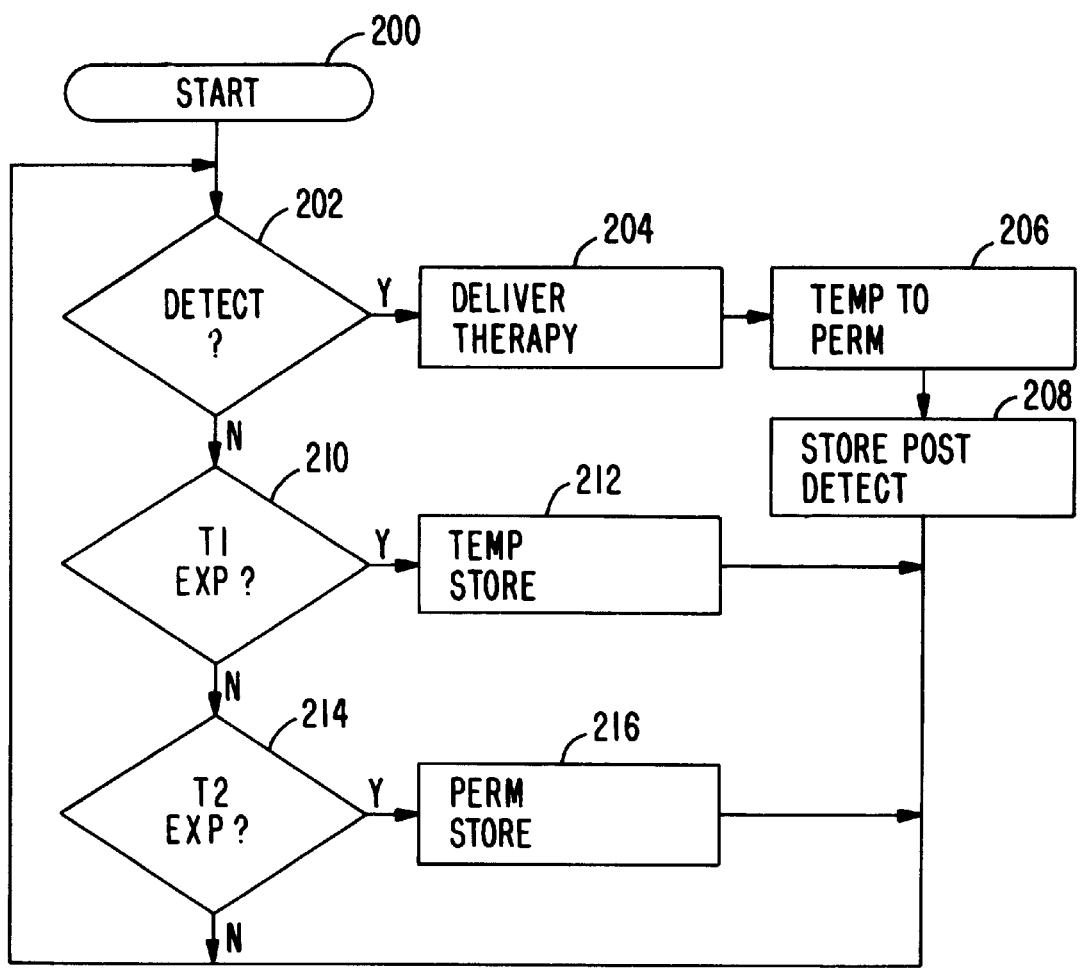
FIG. 3 is a functional flow chart illustrating the operation of a device incorporating the invention.

FIG. 3 is a simplified flow chart summarizing the general operation of the tachycardia/fibrillation discrimination functions that may be performed in the device illustrated in FIG. 2. FIG. 3 is intended to functionally represent that portion of the software employed by microprocessor 524 (FIG. 2) which implements the electrogram and/or sensor record storage function.

FIG. 3 is a functional flow chart illustrating the overall operation of the portion of the software associated with microprocessor 524 which controls storage of electrocardiogram and/or sensor output records. After initialization at 200, the device waits until the detection of an arrhythmia at 202, the expiration of a relatively short first time period, for example one minute or fifteen minutes as discussed above at 210 or the expiration of a second and longer time interval T2 at 214 which may be for example one day or one week, as discussed above. If a tachyarrhythmia is detected at 202, the device delivers therapy at 204, transfers one or more temporarily stored electrogram or sensor output records to permanent memory at 206 and may optionally initiate storage of post detection electrocardiogram records at 208. It should be understood that steps 204, 206 and 208 may occur in any order following detection of an arrhythmia.

In the absence of a detected arrhythmia, on expiration of first time interval T1 at 210, the microprocessor 526 (FIG. 2) initiates temporary storage of an electrocardiogram and/or sensor output record at 212. Typically, the stored record will extend over a pre-defined, relatively short time period, for example five seconds. Because the duration of the stored record is short relative to the duration of time period T1, a substantial reduction in current drain is achieved as compared to a more conventional device employing a looping memory and a continuously activated amplifier. As discussed above, the device may store one or more electrocardiogram strips temporarily in random access memory 526 (FIG. 2), with the most recent record being stored over the oldest temporarily stored record.

In response to expiration of the second, longer time interval T2 at 214, the device may optionally permanently store one or more electrocardiogram and/or sensor records at 215. Storage of the electrocardiogram and/or sensor records may be accomplished either by creating a new record for permanent storage on expiration of time interval T2 or by transferring one or more temporarily stored electrocardiogram and/or sensor output records previously acquired to permanent storage.

As discussed above, in devices employing the present invention, it is envisioned that additional information will be stored in conjunction with detected arrhythmias. The stored electrogram and/or sensor output records may be used in conjunction with this additional stored information related to specific detected arrhythmia episodes to assist the physician in monitoring the patient's condition and evaluating the performance of the device. Similarly, the electrogram and/or sensor records stored at longer intervals corresponding to time interval T2 can provide the physician with a longer term record indicative of the patient's underlying condition.

It should be recognized that although the disclosed embodiment deals with electrograms sensed in and arrhythmias detected in the lower chambers or ventricles of the heart, the invention may be usefully practiced in the context of the upper chambers or atria of the heart, which are also prone to tachycardia and fibrillation in some patients.

The present invention is believed to be readily applicable in the context of any of the various types of implantable pacemakers, cardioverter/defibrillators, or monitoring devices presently available. In the context of a cardiac pacemaker or implantable monitor, detection of an arrhythmia may not trigger delivery of therapy. However, the stored electrogram segments in conjunction with information as to the detected arrhythmias are still believed valuable in conjunction with monitoring the patient's condition.

In addition, while the therapies discussed in conjunction with the disclosed embodiment generally relate to delivery of electrical pulses, it should be understood that the invention may be usefully practiced in conjunction with any device adapted to deliver differing therapies for tachycardia and fibrillation, including drug therapies, non-pulsatile electrical therapies, and any other such therapies as may be implemented in such devices as their development progresses, whether applied directly to the heart or systemically.

Similarly, it is believed the invention may also be adaptable to implantable devices employing other forms of physiologic monitoring, not related to the functioning of the heart, such as implantable drug dispensers, implantable nerve stimulators, implantable muscle stimulators, and the like. In all such cases, a reduction of current drain associated with monitoring of physiological parameters according to the present invention may still be beneficial. It should be understood that the present invention, while particularly adapted for use in or in conjunction with an implantable device may also in some cases be usefully practiced in conjunction with a non-implantable device, in a device which, for example only treats fibrillation or only treats tachycardia, or even in a device adapted primarily for diagnostic purposes.

In conjunction with above application, I claim:

1. An implantable medical device, comprising:
   means for sensing a physiologic parameter;
   means for periodically activating said sensing means for first time intervals, responsive to expirations of second, substantially longer time intervals;
   means for temporarily storing values indicative of said sensed physiologic parameter during said first time intervals;
   means for detection of a physiologic event as a function of values of said physiologic parameter occurring during said second time intervals; and
   means responsive to detection of said physiologic event by said event detection means as a function of values of said physiologic parameter occurring during one of said second time intervals, for permanently storing said values temporarily stored during a preceding one of said first time intervals.

2. A device according to claim 1, further comprising means for transmitting said permanently stored values to a receiver external of the implanted device.

3. A device according to claim 1 or claim 2 wherein said detecting means comprises an arrhythmia detector.

4. A device according to claim 3 wherein said physiological sensor comprises a sense amplifier.

5. A device according to claim 1 or claim 2 further comprising means for triggering permanent storage of values indicative of said physiologic parameter in response to expiration of third time intervals substantially longer than said second time intervals.

6. A device according to claim 5 wherein said means for triggering storage comprises means for triggering permanent storage of said temporarily stored values indicative of said sensed physiologic parameters.

7. A method of monitoring a physiologic parameter in conjunction with a physiological event, comprising:
   implanting a monitoring device comprising means for sensing said physiologic parameter and means for detecting said physiologic event in a patient's body;
   periodically activating said sensing means for a first time interval, responsive to expirations of second, substantially longer time intervals;
   temporarily storing in said monitoring device values indicative of said sensed physiologic parameter during said first time intervals;
   monitoring said physiological parameter to detect occurrences of said physiologic event as a function of values of said physiologic parameter occurring during said second time intervals; and
   responsive to detection of said physiologic event as a function of values of said physiologic parameter occurring during one of said second time intervals, permanently storing said temporarily stored values, stored during a preceding one of said first time intervals, in said monitoring device.

8. A method according to claim 7, further comprising transmitting said permanently stored values to a receiver external of the patient.

9. A method according to claim 7 or claim 8 wherein said permanently storing step comprises storing said temporarily stored values in response to a detected arrhythmia.

10. A method according to claim 9 wherein said sensing step comprises sensing electrical signals in said patient's body.

11. A method according to claim 7 or claim 8 further comprising permanently storing values indicative of said physiologic parameter in said monitoring device in response to expiration of third time intervals substantially longer than said second time intervals.

12. A device according to claim 7 or claim 8 further comprising permanently storing said temporarily stored values indicative of said physiologic parameter in said monitoring device in response to expiration of third time intervals substantially longer than said second time intervals.

* * * * *